United States Patent
Horiuchi (10) Patent No.: US 9,355,124 B2
(45) Date of Patent: May 31, 2016

(54) WRITTEN EXPERT OPINION OF DIAMOND AND METHOD OF PREPARING THE SAME

(71) Applicant: CENTRAL GEM LABORATORY, Tokyo (JP)

(72) Inventor: Nobuo Horiuchi, Tokyo (JP)

(73) Assignee: CENTRAL GEM LABORATORY, Tokyo (JP)

( * ) Notice: Subject to any disclaimer, the term of this patent is extended or adjusted under 35 U.S.C. 154(b) by 0 days.

(21) Appl. No.: 14/786,961

(22) PCT Filed: Apr. 26, 2013

(86) PCT No.: PCT/JP2013/062455
§ 371 (c)(1),
(2) Date: Oct. 23, 2015

(87) PCT Pub. No.: WO2014/174680
PCT Pub. Date: Oct. 30, 2014

(65) Prior Publication Data
US 2016/0070723 A1    Mar. 10, 2016

(51) Int. Cl.
| | | |
|---|---|---|
| *G06F 17/00* | (2006.01) | |
| *G06F 17/30* | (2006.01) | |
| *G01N 21/87* | (2006.01) | |
| *G01B 11/02* | (2006.01) | |
| *G06K 19/06* | (2006.01) | |

(52) U.S. Cl.
CPC .......... *G06F 17/30265* (2013.01); *G01B 11/02* (2013.01); *G01N 21/87* (2013.01); *G06K 19/06028* (2013.01); *G06K 19/06037* (2013.01)

(58) Field of Classification Search
CPC .......... G01N 21/87; G01N 2021/0118; G06Q 30/0623; G06Q 30/0631; G06Q 40/04; G06Q 40/06
USPC .......................................... 235/375; 705/500
See application file for complete search history.

(56) References Cited

U.S. PATENT DOCUMENTS

| | | | | |
|---|---|---|---|---|
| 6,304,853 | B1 * | 10/2001 | Malnekoff | G01N 21/87 705/27.1 |
| 7,414,709 | B2 * | 8/2008 | Wagner | G01N 21/87 356/30 |
| 8,239,211 | B2 * | 8/2012 | Feldman | G01N 21/87 705/1.1 |

\* cited by examiner

*Primary Examiner* — Seung Lee
(74) *Attorney, Agent, or Firm* — Hedman & Costigan, P.C.; James V. Costigan; Kathleen A. Costigan (57) ABSTRACT

The invention includes: a barcode for reading a management number and measurement inspection company information of a polished mined diamond; a two-dimensional code for reading 4C information bound to the management number, the size information of the diamond, and optical virtual reflected images in the respective cases of the presence and absence of a color filter of the diamond created by CG software; and a field for outputting and displaying the 4C information output and displayed from the two-dimensional code and a size display field of the diamond, wherein the optical virtual reflected image in the absence of the color filter and the optical virtual reflected image in the presence of the color filter are output and displayed from the two-dimensional code and the computer database.

3 Claims, 11 Drawing Sheets

13, 1, 17, VACUUM, 15, 14, 16

(b)

1, 17, DIMENSION OF DIAMOND, ACCURATE DIMENSION OF STAGE

WRITTEN EXPERT OPINION OF DIAMOND AND METHOD OF PREPARING THE SAME

TECHNICAL FIELD

According to the present invention, when measuring various items such as carat, color, clarity, and cut (4C) and the color origin of polish-finished mined diamonds in lot units or in single units, each worker previously registers a measurer by performing fingerprint registration or the like on a computer and thereafter uses a barcode reader to read a barcode storing information such as the serial number of the diamond and the company name or the like, wherein the diamond is measured by carat (weight) under a specified management number, and the measurement information is stored in a computer database and a two-dimensional code. In this manner, the next measurer performs the fingerprint registration or the like on the computer and then measurement information is stored in the computer database and the two-dimensional code under the management number recorded in the barcode. The measurement information is stored and managed in the computer database (referred to as "DB") and the two-dimensional code and a CG image of the three-dimensional shape of the diamond is created through software of computer graphics (CG) on the basis of subsequent various dimension measurements. Optical virtual reflected images, which have been created by CG software in the respective cases of the presence and absence of a color filter for the CG image of the three-dimensional shape of the diamond, are output and displayed on a written expert opinion.

In addition, the CG image of the three-dimensional shape of the diamond is stored in the computer DB and various data information such as clarity, color, cut, and carat (4C) of the diamond is stored into the computer DB. The optical virtual reflected images of the diamond created by CG software in the respective cases of the presence and absence of the color filter are created on the basis of the fundamental laws of geometrical optics. For example, in the case of a round brilliant cut diamond, light incident from the pavilion main facet side is reflected on a table top and is formed into a heart-shaped pattern image and light incident from the table crown side is reflected on a pavilion surface and is formed into an arrow-shaped pattern image, thereby enabling the acquirement of optical virtual reflected images by the CG software in the respective cases of the presence and absence of the color filter of Heart & Cupid®.

BACKGROUND ART

In a conventional diamond written expert opinion, a number identifying a target diamond is appended to the diamond. For the diamond with the identification number appended, for example, in the case of a round brilliant cut diamond, light is caused to be incident from the pavilion side with the pavilion on the upper side and the crown on the lower side to acquire a photographic image of heart shapes which is a reflected image from the table top and the facet surfaces on the crown side, while light incident from the crown side is caused to be reflected on the facet surfaces on the lower pavilion side with the crown on the upper side and the pavilion on the lower side and a pattern image of arrow shapes with light emitting to the crown side is photographed, and then the photographic images have been pasted to predetermined positions of a written expert opinion.

Moreover, out of the diamond appraising method and device in Patent Document 1, which is another conventional art document, the diamond appraising method includes the steps of: (1) setting and fixing a diamond to be appraised on a measurement stage which is rotatable by driving means; (2) irradiating the diamond to be appraised with light by using a light source; (3) rotating the measurement stage by a predetermined angle by controlling the driving means by using a cut evaluation measurement computer; (4) detecting a silhouette image of the diamond to be appraised by using a camera set on the opposite side to the light source for the diamond to be appraised and capturing and storing the image data of the detected silhouette image of the diamond to be appraised into the cut evaluation measurement computer; (5) capturing and storing the image data of the silhouette image of the diamond to be appraised taken from a plurality of predetermined directions into the cut evaluation measurement computer by repeating the steps (3) and (4) in this order more than once; (6) evaluating the cut of the diamond to be appraised by using the image data of the silhouette image stored in the cut evaluation measurement computer and storing the cut evaluation data into a database so that the cut evaluation data corresponds to the diamond to be appraised; (7) measuring the weight and color of the diamond to be appraised by using a weight and color measuring device and storing the measurement data so that the measurement data corresponds to the diamond to be appraised; (8) photographing the diamond to be appraised by using a photographic image capture device and storing the photographic image data so that the photographic image data corresponds to the diamond to be appraised; (9) creating image data of an image obtained by graphing the cut evaluation data and storing the image data into the database; and (10) printing a written expert opinion in a predetermined format on the basis of the data acquired through the steps (6), (7), (8), and (9) (Patent Document 1).

Moreover, paragraph 0013 of Patent Document 1 includes the following description: (13) photographing the diamond to be appraised by using the photographic image capture device, inputting the photographic image data into the database, and storing the photographic image data with the same management number appended so that the photographic image data corresponds to the diamond to be appraised.

Furthermore, in the positions on the diamond written expert opinion in FIG. 8 of Patent Document 1, a photographic image and graphed image data created on the basis of the cut evaluation data of the diamond are illustrated. As described in paragraph 0006 of the specification of Patent Document 1, there is a description of storing a silhouette image taken by a camera set in a position on the opposite side of the diamond to the light source into the computer database and then printing the photographic image and the graphed image data created on the basis of the cut evaluation data on the written expert opinion.

CITATION LIST

Patent Documents

Patent Document 1: Japanese Patent Application Laid-Open No. 9-273994

SUMMARY OF THE INVENTION

Problems to be Solved by the Invention

In the conventional example described first among the aforementioned conventional techniques, a plurality of diamonds are managed in lot units and, for each diamond corresponding to the identification number, pattern images acquired by reflecting light on the respective facet surfaces by light irradiation are photographed and the photographs of the heart-shaped and arrow-shaped pattern images have been pasted in predetermined positions of the written expert opinion.

Moreover, in the aforementioned conventional example described first, a person pastes the photographs to the written expert opinion with verifying the identification numbers corresponding to the individual diamonds one by one while looking at a slip. The conventional example, however, has had the risk of occurrence of a human paste error such as pasting the photograph of a diamond not corresponding to the identification number, in spite of checking the number when pasting the photograph.

On the other hand, in paragraph 0013 of the specification of Patent Document 1, there is the following description: (11) sending the cut evaluation data acquired in step (10) described above to the database and storing the cut evaluation data with a management number appended so that the cut evaluation data corresponds to the diamond to be appraised; (12) inputting measurement data obtained by a device for measuring appraisal items except cut evaluation (for example, weight and color measurement data of the diamond to be appraised obtained by a weight and color measuring device) into the database and storing the measurement data with the same management number appended so that the measurement data corresponds to the diamond to be appraised, where the appraisal items except the cut evaluation are color, clarity, weight, fluorescence, and the like; and (13) photographing the diamond to be appraised by using the photographic image capture device, inputting the photographic image data into the database, and storing the photographic image data with the same management number appended so that the photographic image data corresponds to the diamond to be appraised.

As the advantageous effects of the invention described in Patent Document 1, paragraph 0019 of the specification includes the description: according to the method and apparatus for appraising a diamond of the invention, cut evaluation data, appraisement data except cut evaluation, diamond photographic image data, and image data of various images obtained by graphing the cut evaluation data are digitally stored and managed with the same management number appended in a series of appraisement works from cut evaluation to preparation of the written expert opinion, thereby eliminating the complication of practically taking an image photograph and managing the photographs separately from the cut evaluation data and preventing an occurrence of a paste error of the image photograph, by which the reliability of the appraisal is improved, written expert opinions including images can be printed at a time and thus the working hours are reduced, the various images from the graphed cut evaluation data always maintain the same image quality, and the layout, configuration, and color of the written expert opinion can be arbitrarily changed.

In the invention described in Patent Document 1, however, in all steps of: (11) sending the cut evaluation data acquired in step (10) described above to the database and storing the cut evaluation data with a management number appended so that the cut evaluation data corresponds to the diamond to be appraised; (12) inputting measurement data obtained by a device for measuring appraisal items except cut evaluation (for example, weight and color measurement data of the diamond to be appraised obtained by a weight and color measuring device) into the database and storing the measurement data with the same management number appended so that the measurement data corresponds to the diamond to be appraised; and (13) photographing the diamond to be appraised by using the photographic image capture device, inputting the photographic image data into the database, and storing the photographic image data with the same management number appended so that the photographic image data corresponds to the diamond to be appraised in paragraph 0013, a worker performs: (a) an input work of appending the management number to the cut evaluation data; (b) an input work of appending the same management number to the measurement data; and (c) an input work of appending the same management number to the photographic image data, and thus the worker needs to perform the input work of appending the same management number for each of the works (a), (b), and (c). This causes a problem such that an input error is difficult to avoid as long as a human performs the input during the input work of the management number for each work. Such input error is an issue affecting the credit of dealers who deal in expensive gems.

In order to solve the above problem, the present invention uses a computer database to manage and store a barcode including a serial number (management number) for identifying a diamond and information on a measurement inspection company and a two-dimensional code including 4C information on the diamond and information such as optical virtual reflected images or the like created by CG software in the respective cases of the presence and absence of a color filter in a virtual reflected image display of the diamond, wherein, with respect to input-output information of each diamond, information including the serial number (management number) and the measurement inspection company is managed by the barcode and the computer database and 4C information of the diamond and the optical virtual reflected images and the like of the diamond created by CG software are managed by the two-dimensional code and the computer database, and these pieces of information are input or output to or from the computer via a reader, thereby completely eliminating the trouble caused by a human error in inputting the management number, which has conventionally occurred.

Moreover, the present invention does not employ the photographic images of patterns acquired by actual light irradiation, which require skills, time, and effort for various cut types of diamonds. Instead, focusing attention on that the refractive index of the diamond stays constant, the present invention creates optical virtual light emission pattern images based on the fundamental laws of geometrical optics in the form of CG images by using CG software in order to eliminate the conventional complicated photographing works requiring skills such as creating reflected images using photographs, so that simple and accurate optical virtual reflected images of the diamond can be output and displayed on a written expert opinion in the respective cases of the presence and absence of a color filter through CG software.

More specifically, according to the present invention, it is possible to create a three-dimensional image of the diamond by CG software on the basis of numerical values acquired by measuring the respective regions of the diamond shape by using a dimension measuring device, to store the three-dimensional image of the diamond in the computer database, to rapidly and precisely create the optical virtual reflected images of the diamond, in the respective cases of the presence and absence of the color filter, for example, viewed from the crown side and acquired by CG software and an optical virtual reflected image, in the case of the presence of the color filter, viewed from the pavilion side and acquired by CG software, relative to the three-dimensional image of the diamond created by the CG software, and to output and display the optical virtual reflected images on a written expert opinion.

The present invention provides a reliable diamond written expert opinion and a method of preparing the written expert opinion, wherein a management number and a measurement inspection company of a diamond are read by using a barcode reader; various measurement data associated with the management number are recorded into a computer database; optical virtual reflected images of the diamond created by CG software in the respective cases of the presence and absence of a color filter are also associated with the management number and stored in the computer database; and a dealer, a purchaser, and the like of the diamond are able to glance at the diamond cut type as an optical virtual reflected image, which depends on the presence or absence of the color filter, viewed from, for example, the crown side and viewed from the pavilion side on the written expert opinion.

Means for Solving the Problems

According to the present invention, there is provided a diamond written expert opinion includes: a barcode for reading a management number and measurement inspection company information of a polished mined diamond; a two-dimensional code for reading 4C (carat, color, clarity, and cut) information bound to the management number, the size information of the diamond, and optical virtual reflected images of the diamond created by CG software in the respective cases of the presence and absence of a color filter; a field for outputting and displaying the 4C information output and displayed from the two-dimensional code; and a size display field of the diamond, wherein the optical virtual reflected image in the absence of the color filter and the optical virtual reflected image in the presence of the color filter are output and displayed from the two-dimensional code and the computer database.

There is provided the diamond written expert opinion according to claim 1, wherein: the mined diamond is a round brilliant cut diamond; the optical virtual reflected images created by the CG software include optical virtual arrow-shaped reflected images created by CG software in the respective cases of the presence and absence of the color filter when virtual light is incident from the crown side of the diamond and an optical virtual heart-shaped reflected image created by CG software in the case of the presence of the color filter when virtual light is incident from the pavilion side.

A method of preparing a diamond written expert opinion according to the present invention includes the steps of: reading a barcode including a management number of a diamond and measurement inspection company information and a two-dimensional code stored in a computer database by using a reader; taking a silhouette image of the diamond by a CCD camera in order to measure the dimensions of the diamond managed by the same management number; creating a three-dimensional shape image of the diamond by CG software on the basis of the diamond images which have been taken; and outputting and displaying an optical virtual reflected image from the flat surface side of the three-dimensional shape image created by the CG software on the basis of the three-dimensional shape image of the diamond and optical virtual reflected images depending on the presence or absence of the color filter when viewed from directly above with the bottom surface facing up in a display field of the written expert opinion.

Advantageous Effect of the Invention

According to the present invention, a management number is appended to each of the mined diamonds managed in lot units or individually for the management of the plurality of polished mined diamonds, the management number is managed by a computer database and by a barcode output from the database, and a two-dimensional code output from the database is displayed on a written expert opinion as 4C information and optical virtual reflected images according to the presence or absence of a color filter when viewed from directly above with the flat surface facing up and with the bottom surface facing up in the three-dimensional shape of the diamond created by CG software with respect to the diamonds of the same management number. This completely eliminates troubles caused by a human error in inputting the management number or individual management numbers as has been conventionally caused and enables the acquisition of optical virtual reflected images according to the presence or absence of the color filter no less smart than photographic images obtained by skill and high photographing technique, thereby achieving high level of quality control and further increasing the reliability.

Moreover, photographing diamonds for various cut types is performed only for identifying the three-dimensional shape of a diamond. For subsequent identification of the three-dimensional shape of the diamond, the optical virtual reflected images according to the presence or absence of the color filter are created from the three-dimensional shape of the diamond created by CG software. Therefore, it is unnecessary to employ a photographic image obtained by light irradiation which requires skill, time, and effort as has been conventionally employed.

Further, the optical virtual reflected images in the respective cases of the presence and absence of the color filter are created by CG software according to a construction method based on the fundamental laws of geometrical optics focusing attention on that the refractive index of the diamond stays constant. This solves the problem of the complicated photographing work for taking reflected images of photographs which requires skill, time, and effort, by which precise optical virtual reflected images are easily obtained by CG software for the respective cases of the presence and absence of the color filter and therefore leave a vivid impression on a viewer and give an aesthetic view to the viewer.

Furthermore, as a result of acquiring arrow-shaped optical virtual pattern images in the respective cases of the presence and absence of the color filter by CG software, which have been acquired by the emission of optical virtual light on the table top and the facet surface on the crown side after the reflection on different two facet surfaces on the pavilion side relative to the optical virtual incident light from the table crown side of, for example, a round brilliant cut diamond, it is possible to create optical virtual light emission pattern images which are substantially equivalent to photographs. Moreover, in the case of the presence of the color filter, the selective absorption of light causes the arrow portions to be white and the outlines of the arrow portions to be blue or the like, thereby increasing the contrast of the image and thus increasing the commodity value. In addition, also in the absence of the color filter by CG software which is acquired by the emission of optical virtual light from the pavilion side after the reflection on the table top and the facet surface on the crown side relative to the optical virtual incident light from the pavilion side, a heart-shaped optical virtual pattern image is created and an optical virtual pattern image substantially equivalent to a photograph can be easily created. Specifically, it is unnecessary to perform the conventional time-consuming works requiring skill such as work preparation and reshooting when photographing reflected pattern images of the diamond using light reflection.

Moreover, according to the present invention, the written expert opinion includes a barcode for reading information on a management number and a measurement inspection company and a two-dimensional code for reading the 4C (carat, color, clarity, and cut) information and optical virtual reflected images of the diamond created by CG software. Therefore, the present invention has advantageous effects such that a dealer who purchased the diamond from the measurement inspection company can share the same diamond information as that of the measurement inspection company via online of a computer network and the purchasing company of the diamond is able to carry out unique commodity management on the basis of the information on the barcode and the two-dimensional code, thus further increasing the reliability in the quality control of the dealer from an end user.

In addition, even if an expensive diamond were stolen or the like, it is possible to find the stolen diamond at home or abroad and to discover the culprit from the stolen diamond in cooperation with the measurement inspection company via online by previously copying the barcode and the two-dimensional code on the written expert opinion or storing the barcode and the two-dimensional code in a computer, thereby enabling contribution to criminal investigations so as to have an anticrime effect.

MODE FOR CARRYING OUT THE INVENTION

Figure 2:
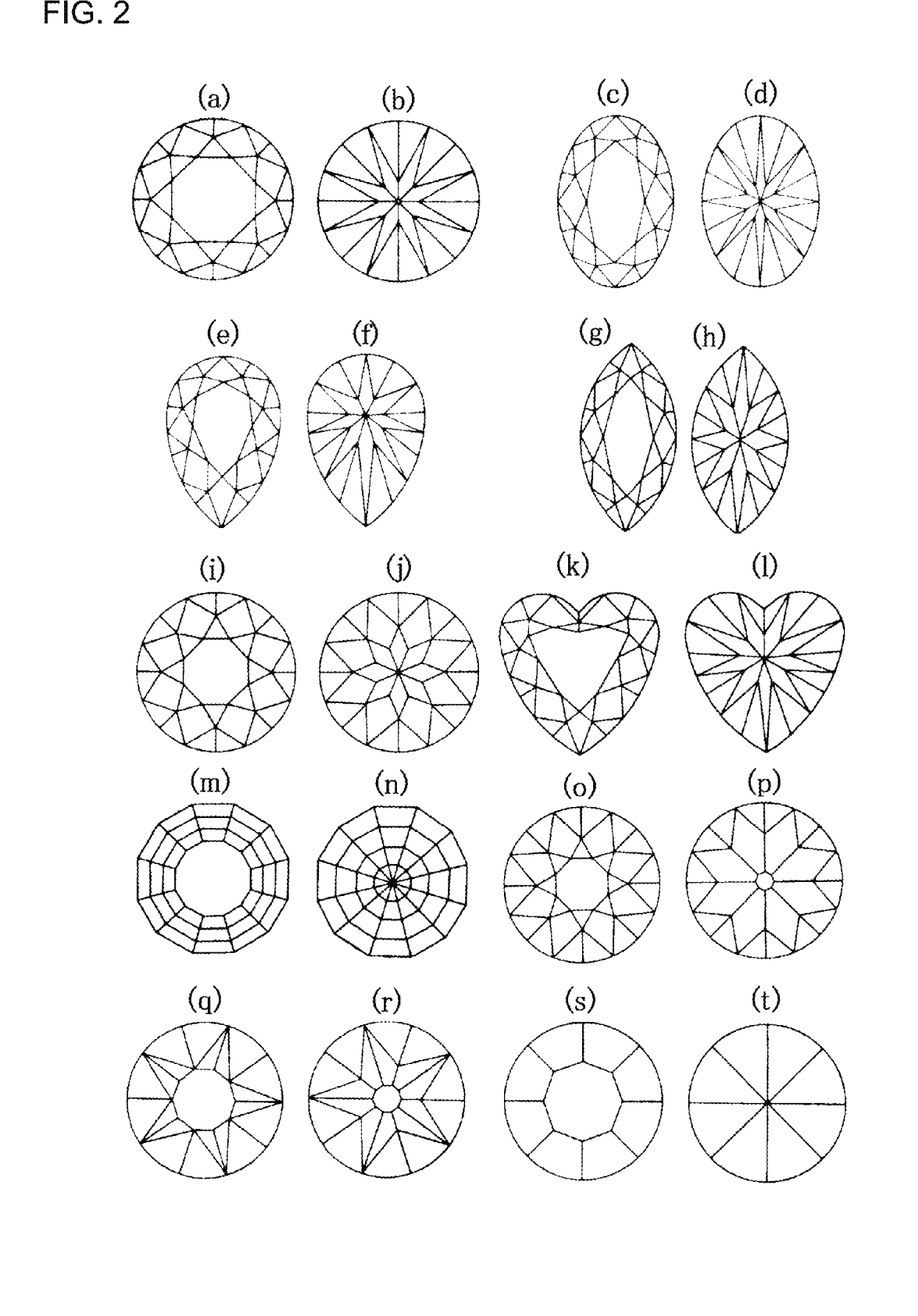
FIG. 2 is a diagram illustrating the top views and the bottom views of various diamonds to be appraised according to the present invention: (a) the top view and (b) the bottom view to (s) the top view and (t) the bottom view.
Figure 3:
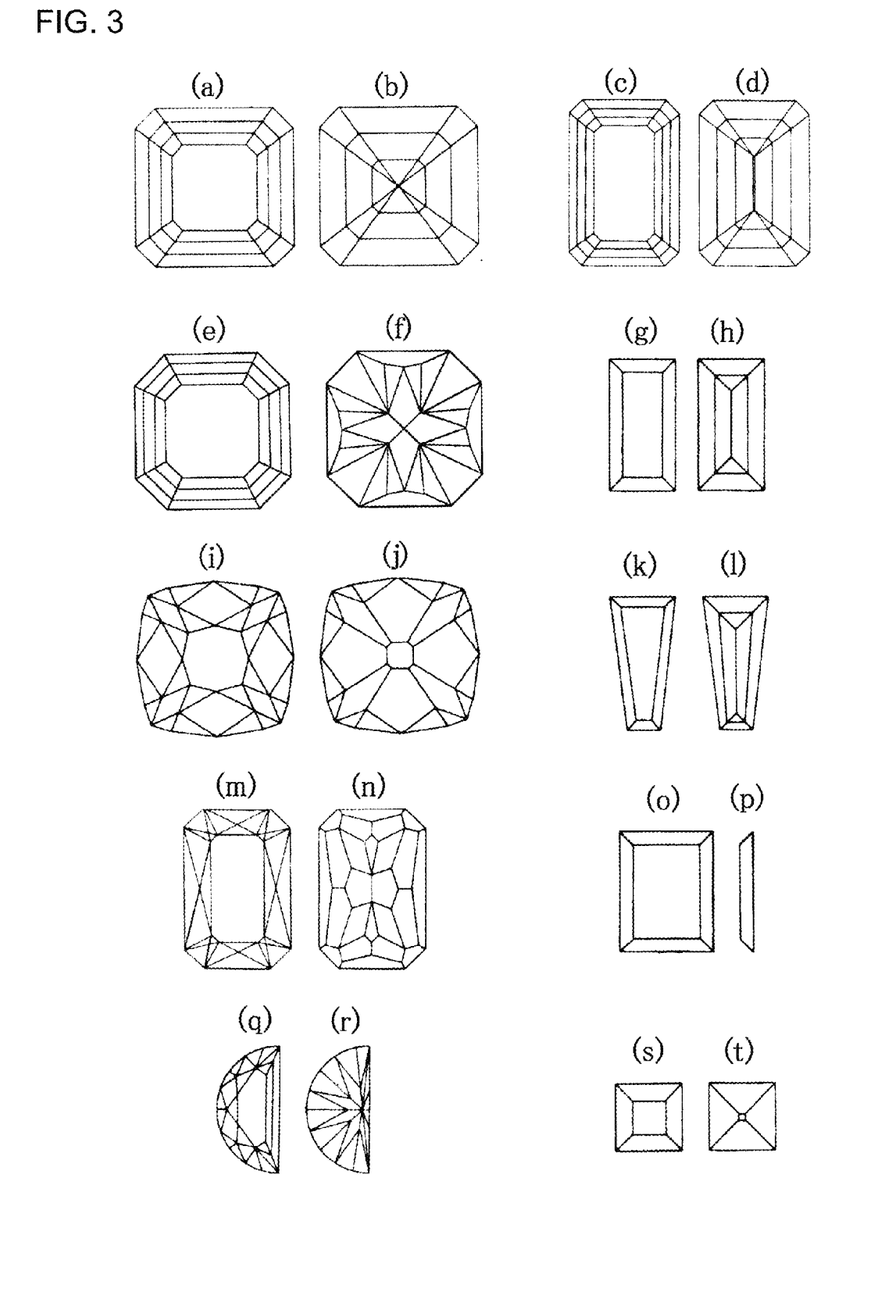
FIG. 3 is a diagram illustrating the top views and the bottom views of various diamonds to be appraised according to the present invention: (a) the top view and (b) the bottom view to (s) the top view and (t) the bottom view.

In the present invention, diamonds to be measured in dimensions as polished mined diamonds are classified into the cut types described below. In each cut type, a top view viewed from the upper side is illustrated on the left side and a bottom view viewed from the lower side is illustrated on the right side. FIGS. 2(a) and 2(b) illustrate a round brilliant cut type. FIGS. 2(c) and 2(d) illustrate an oval brilliant cut type. FIGS. 2(e) and 2(f) illustrate a pear-shaped brilliant cut type. FIGS. 2(g) and 2(h) illustrate a marquise brilliant cut type. FIGS. 2(i) and 2(j) illustrate a zircon-cut type. FIGS. 2(k) and 2(l) illustrate a heart-shaped brilliant cut type. FIGS. 2(m) and 2(n) illustrate a trap brilliant cut type. FIGS. 2(o) and 2(p) illustrate an Old European cut type. FIGS. 2(q) and 2(r) illustrate a split brilliant cut type. FIGS. 2(s) and 2(t) illustrate a single-cut type. FIGS. 3(a) and 3(b) illustrate a square emerald-cut type. FIGS. 3(c) and 3(d) illustrate an emerald-cut type. FIGS. 3(e) and 3(f) illustrate a baryon-cut type. FIGS. 3(g) and 3(h) illustrate a baguette-cut type. FIGS. 3(i) and 3(j) illustrate an old mine cut type. FIGS. 3(k) and 3(l) illustrate a tapered baguette cut type. FIGS. 3(m) and 3(n) illustrate a scissors cut type. FIGS. 3(o) and 3(p) illustrate a bevel cut type. FIGS. 3(q) and 3(r) illustrate a half-moon cut type. FIGS. 3(s) and 3(t) illustrate a table cut type.

First Embodiment

In this embodiment, a written expert opinion for a round brilliant cut diamonds 1 is described. Although the description is made on the case where the diamonds are managed in lot units in this embodiment, the present invention is also applicable to the management of diamonds in single units.

The management of the round brilliant cut diamonds 1 is performed for each lot and a serial number (hereinafter, referred to as "management number") N which has been input when the weight of each diamond is measured is input to a computer database. A barcode and a two-dimensional code input to the database are each provided with the management number. The first management number of the barcode and the two-dimensional code output from the computer is read by a code reader R and various input information of the diamond related to the subsequent same management number is read by the code reader R for barcodes and two-dimensional codes and then the information is input to the computer. This completely eliminates troubles caused by human input errors. Specifically, the management number of the diamond 1 is read by the code reader R for barcodes and two-dimensional codes and the identity of the diamond is confirmed and all information is input to the database.

Figure 1:
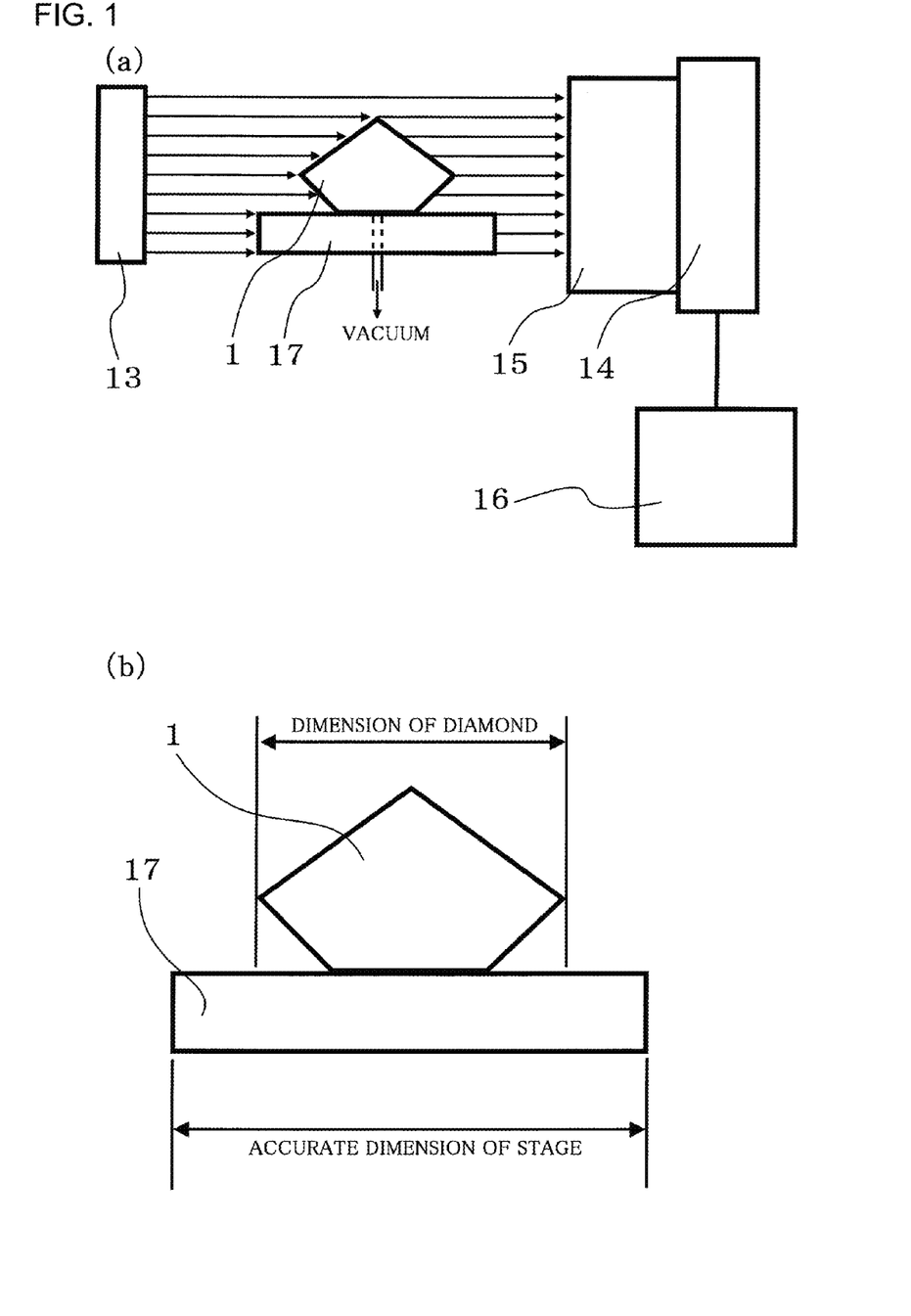
FIG. 1(a) is an explanatory diagram illustrating a diamond dimension measuring device.
FIG. 1(b) is an explanatory diagram illustrating an example of calculating the dimension (diameter) of the diamond with reference to accurate dimensions of a rotary stage.

FIG. 1(a) is an explanatory diagram illustrating a dimension measuring device of a diamond, and FIG. 1(b) is an explanatory diagram illustrating an example of calculating the diameter or the like which is a dimension of the diamond 1 with reference to the accurate dimensions of a rotary stage 17. FIG. 1(a) is a pattern diagram illustrating the principle of dimension measurement of the round brilliant cut diamond 1 (hereinafter, simply referred to as "diamond 1") by using a DiaVision HD (a commodity name).

The diamond 1 is set with the center of the diamond 1 placed in the center position of the rotary stage 17. The diamond 1 is fixed by suction in a suction hole (not illustrated)

provided at the center of the rotary stage 17. The diameter of the rotary stage 17 is managed accurately as the dimension.

Slit laser 18 which is a parallel beam is emitted from a light source 13 illustrated in FIG. 1(a) to the diamond 1 placed on the rotary stage 17. The parallel beam emitted to the diamond 1 passes through the diamond 1 and imaged by a CCD camera 14 through a lens. The imaging information is input to a database 19 of a computer 16. The dimensions of the respective portions of the diamond 1 such as, for example, the dimensions of a table, a star facet, a bezel facet, and an upper girdle facet on the crown side and a girdle, a culet, a pavilion facet, and a lower girdle facet on the pavilion side are each calculated as a ratio relative to the accurate dimension of the rotary stage 17. Similarly, the angles of the respective portions of the diamond 1 are calculated by using a function from the dimensions of the respective surfaces. Although the diamond 1 is rotated in units of 3.6° relative to the rotation angle 360° of the rotary stage 17 which is rotated by a stepping motor (not illustrated) in this embodiment, the rotation angle is not limited to this angle, but may be varied as needed. In this embodiment, there is illustrated a case of measuring the silhouette of the diamond 1 at 100 places by a rotation in units of 3.6°. A three-dimensional image of the diamond 1 is created by CG software on the basis of the dimensions of the respective portions of the diamond 1 and is stored in the database 19 of the computer.

Figure 4:
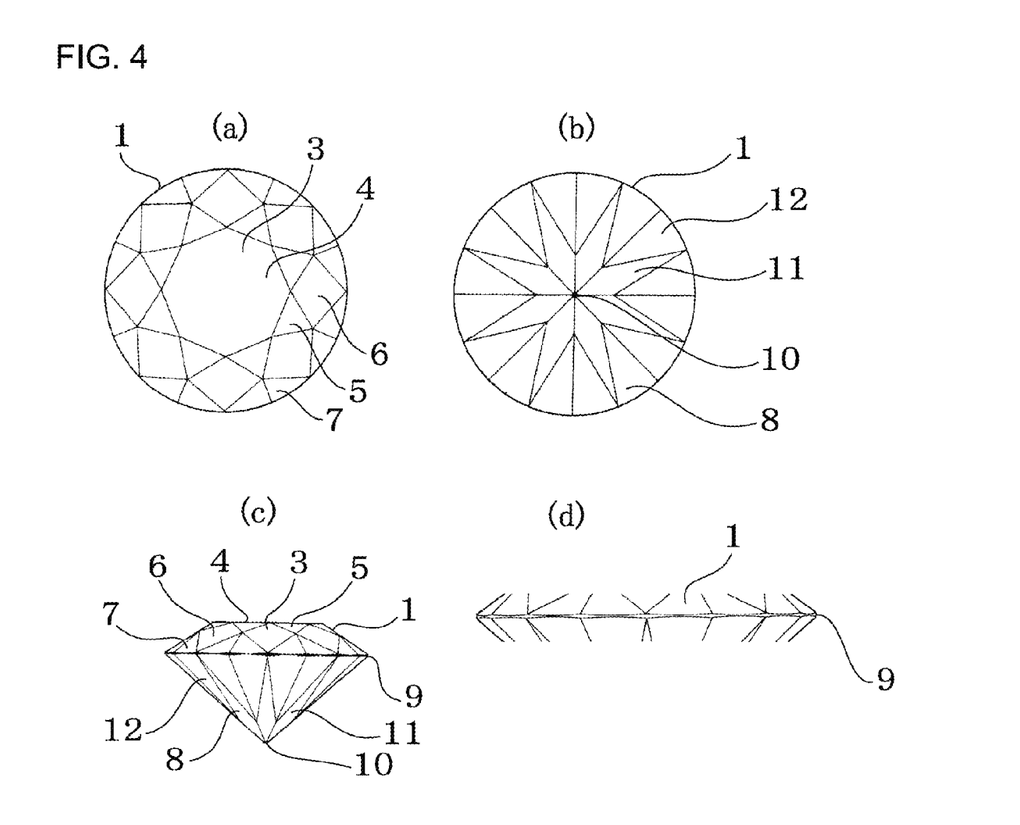
FIGS. 4(a), 4(b), 4(c), and 4(d) are an optical virtual top view, an optical virtual bottom view an optical virtual front view, and a girdle enlarged view, respectively, of a round brilliant cut diamond created by CG software.

FIG. 4(a) is a top view viewed from the upper crown side 3 and FIG. 4(b) is a top view viewed from the lower pavilion side 8. In FIG. 4(a), the upper crown side 3 includes the faces: a table 4, a star facet 5, a bezel facet 6, and an upper girdle facet 7.

The table 4 is finished into an octagon shape with a flat surface. Each star facet 5 is in contact with one of eight sides of the table 4 and is formed of a triangle-shaped inclined surface. Each bezel facet 6 is formed of an inclined surface having an anomalous quadrangle, wherein two sides are in contact with the respective single sides of two star facets 5 and other two sides are between two upper girdle facets 7 with each side in contact with each side of the upper girdle facets 7. The upper girdle facet 7 has a deformed fan-like form with the arcuate portion in contact with the girdle 9. There are 16 upper girdle facets 7 on the same circumference.

Next, in FIG. 4(b), the lower pavilion side 8 has a substantially conical shape, while each facet surface is finished flat. At the lower end of the substantially conical shape, a culet 10 composed of a small circle exists. In each of the eight equal parts of the circle each having a 45-degree angle and passing through the center of the circle, a lancet-shaped pavilion facet 11 is radially formed from the center with the flat surface. In each 45-degree angle part, arcuate lower girdle facets 12 are formed with the pavilion facet 11 therebetween. FIG. 4(c) is a front view of the round brilliant cut diamond 1 created by CG software with the girdle 9 located between the upper crown side 3 and the lower pavilion side 8. In the enlarged view of the girdle 9, substantially rhombic shapes in a horizontal direction are formed continuously in a circumferential direction. FIG. 4(d) is an enlarged view of the girdle 9.

In each of the cases where optical virtual incident light is caused to be incident from directly above with the crown side of the diamond 1 created by CG software facing up and where optical virtual incident light is caused to be incident from directly above with the pavilion side of the diamond 1 facing up, refraction and reflection are repeated by using a construction method based on the fundamental laws of geometrical optics, by which an optical virtual emission from the surface of the diamond is acquired as an optical virtual reflected image which has passed through a color filter by CG software.

Figure 8:
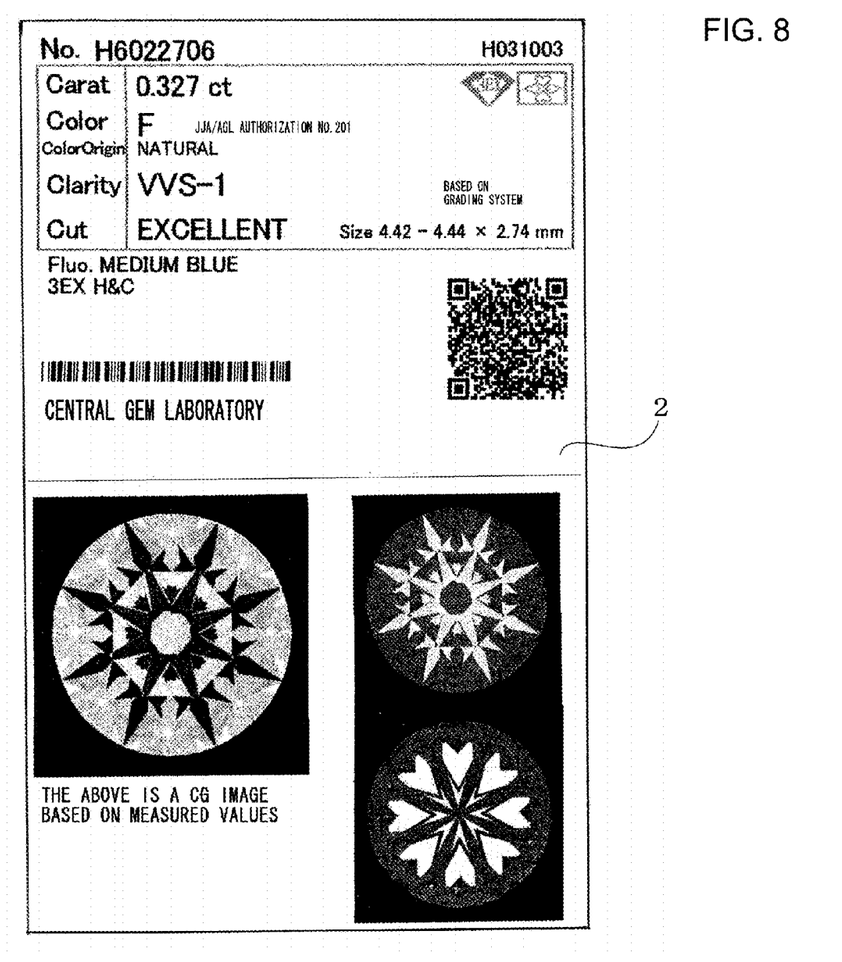
FIG. 8 is a diagram illustrating a barcode, a two-dimensional code, and optical virtual reflected images of a diamond in the respective cases of the presence and absence of a color filter, which are output and displayed on a diamond written expert opinion according to the present invention.
Figure 9:
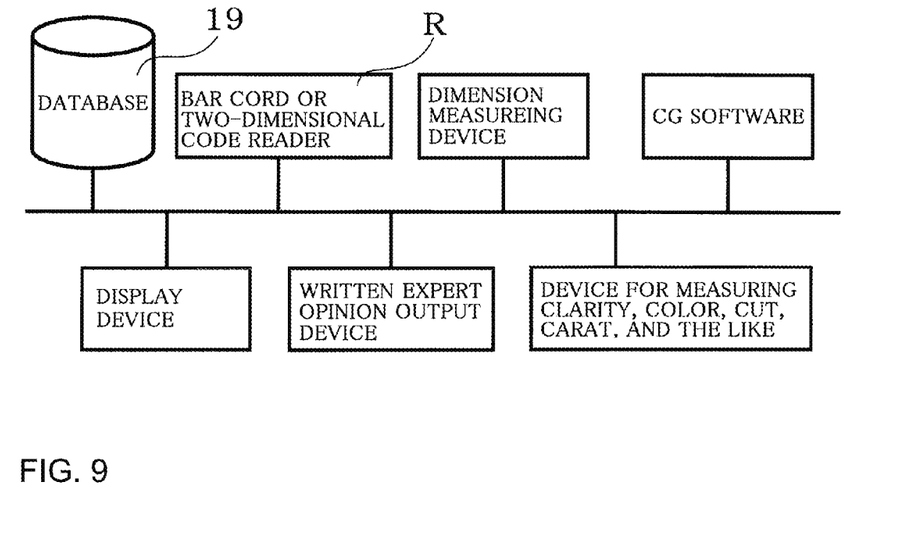
FIG. 9 is a diagram illustrating the structure of a computer which prepares the diamond written expert opinion according to the present invention.
Figure 10:
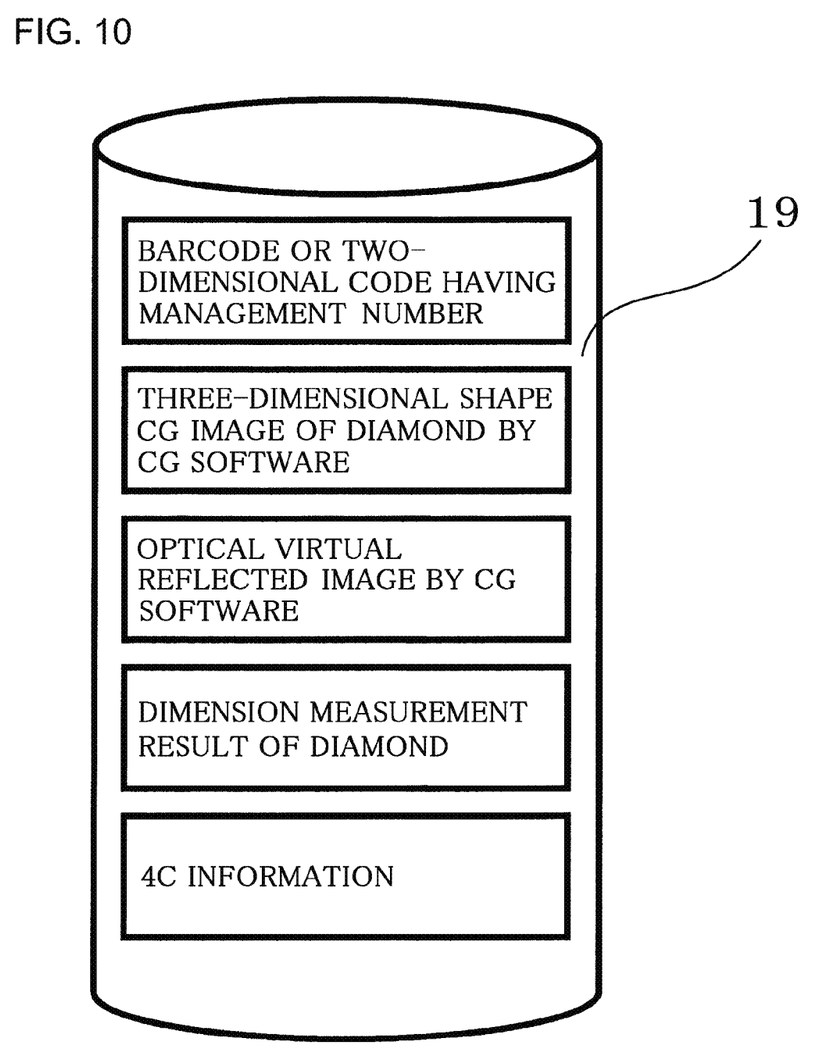
FIG. 10 is a diagram illustrating a database of the computer which prepares the diamond written expert opinion according to the present invention.
Figure 11:
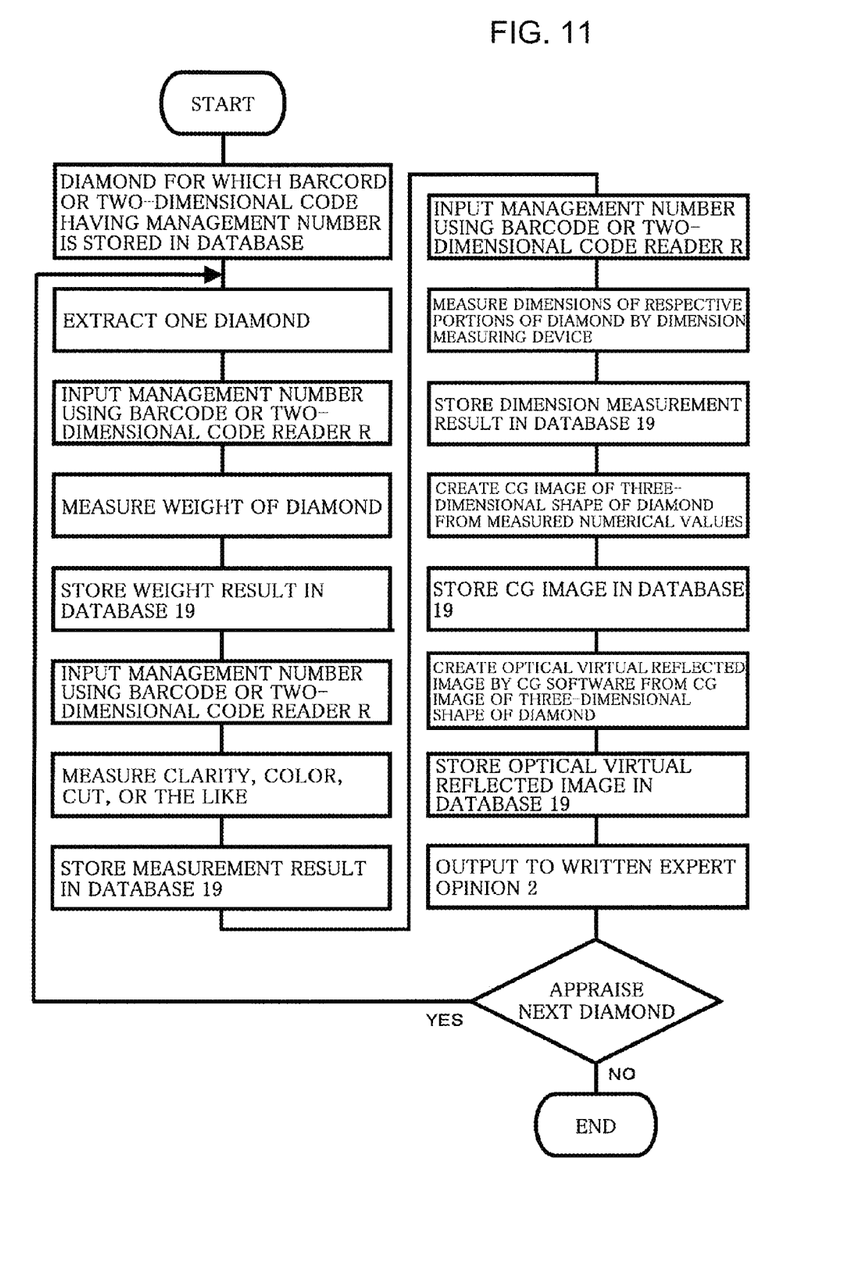
FIG. 11 is a diagram illustrating a flowsheet for preparing the diamond written expert opinion according to the present invention.

When the pavilion is on the upper side, an optical virtual reflected image, which is acquired by optical virtual incidence through the color filter from the pavilion side, has eight heart shapes in a symmetrical manner within the same circle, and this image is output to a written expert opinion 2 by the computer 16. Moreover, when the crown is on the upper side, an optical virtual reflected image, which is acquired by optical virtual light incidence in the respective cases of the presence and absence of the color filter from the crown side, has eight arrow shapes in a symmetrical manner within the same circle. Out of the optical virtual reflected images, the image on the left side is an image in the absence of the color filter and the image in the upper stage on the right side is an image in the presence of the color filter, and these images are output to the written expert opinion 2 by the computer 16 (See FIG. 8).

Figure 5:
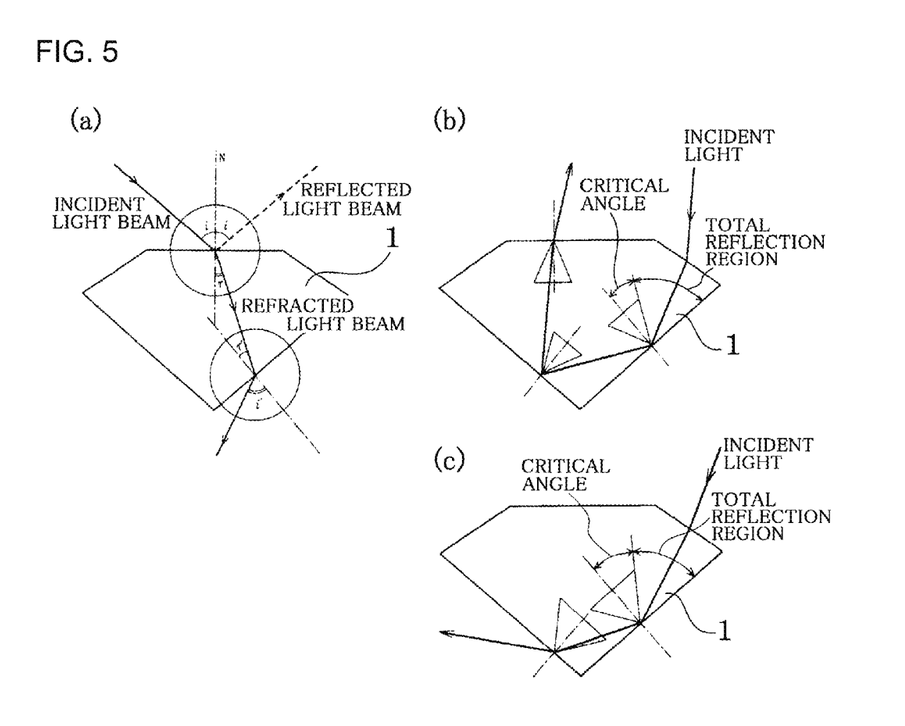
FIG. 5 is an explanatory diagram illustrating an incident light beam, a reflected light beam, a refracted light beam, a critical angle, and a total reflection region of the round brilliant cut diamond.

When light enters the diamond from the air, the following calculation formula is used as illustrated in FIGS. 5(a) to 5(c):

$$n = \sin i / \sin r$$

where n is a refractive index, i is an angle of incidence, and r is an angle of refraction.

When light gets out of the diamond into the air, light gets out to the outside only in the case where the angle of incidence r' is smaller than a critical angle.

The refractive index n of the diamond is 2.417 and the incident light enters the diamond according to the following equation:

$$2.417 = \sin i / \sin r$$

In other words, after the dimensions of the diamond become clear, how the light incident on the diamond is reflected can be exactly calculated.

Figure 6:
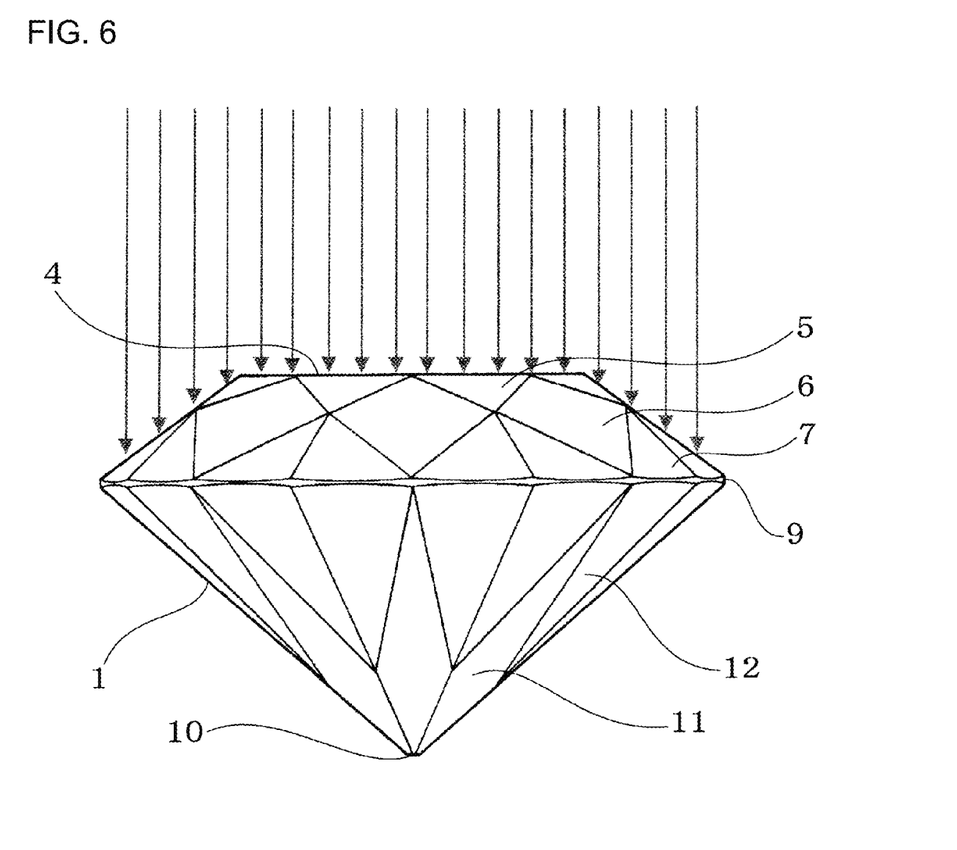
FIG. 6 is a sample drawing of an optical virtual incident light beam entering from the crown side of the round brilliant cut diamond.
Figure 7:
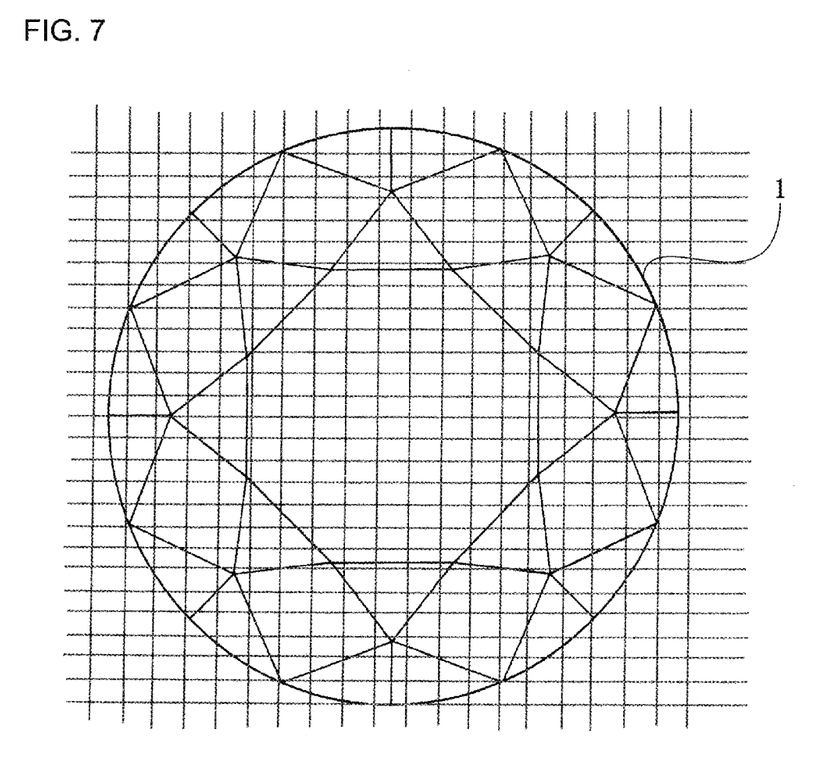
FIG. 7 is a diagram illustrating a top view from the crown side of the round brilliant cut diamond with squares arranged in vertical and horizontal directions in a state before throwing optical virtual light perpendicularly to the squares and tracing the light.

In this embodiment, as illustrated in FIG. 6, it is assumed that an optical virtual luminous flux is formed of 1,000 beams per millimeter. This calculation is made from end to end of the diamond on the basis of the above calculation formula to create an optical virtual reflected image obtained by optical virtual reflected light with respect to the optical virtual incident light on CG of the computer 16. Data on the optical virtual reflected image is stored in the computer database. Note that the number of beams of the optical virtual luminous flux is not limited to 1,000 per millimeter, but the number of beams can be changed as needed.

INDUSTRIAL APPLICABILITY

According to the present invention, with respect to the same diamond, a worker does not need to input a serial number (management number) of the diamond in each process of weight measurement (carat), dimension measurement, or the like, but the worker is only required to cause the code reader to read the management number input in a barcode or a two-dimensional code in various works for the same management number, thereby eliminating input errors of the management number, and the worker only needs to output and display reliable optical virtual reflected images and the like of the diamond created by safe and assured CG software on the written expert opinion, thereby further increasing the reliability of written expert opinions of the whole gem industry. Moreover, a dealer and a gem purchaser are able to check the optical virtual reflected images in the respective cases of the presence and absence of the color filter created by CG software relative to the actual diamond and the optical virtual reflected image of the diamond when viewed from directly above with the bottom view side facing up at a time as a set by looking at the written expert opinion, by which reassured transactions and purchases are accelerated.

DESCRIPTION OF REFERENCE NUMERALS

1 Round brilliant cut diamond
2 Written expert opinion
3 Upper crown side
4 Table
5 Star facet
6 Bezel facet
7 Upper girdle facet
8 Lower pavilion side
9 Girdle
10 Culet
11 Pavilion facet
12 Lower girdle facet
13 Light source
14 CCD camera
15 Lens
16 Computer
17 Rotary stage
18 Slit laser
19 Database
R Bar code or two-dimensional code reader

The invention claimed is:

1. A diamond written expert opinion includes: a barcode for reading a management number and measurement inspection company information of a polished mined diamond; a two-dimensional code for reading 4C (carat, color, clarity, and cut) information bound to the management number, the size information of the diamond, and optical virtual reflected images of the diamond created by CG software in the respective cases of the presence and absence of a color filter; a field for outputting and displaying the 4C information output and displayed from the two-dimensional code; and a size display field of the diamond, wherein the optical virtual reflected image in the absence of the color filter and the optical virtual reflected image in the presence of the color filter are output and displayed from the two-dimensional code and the computer database.

2. The diamond written expert opinion according to claim 1, wherein: the mined diamond is a round brilliant cut diamond; the optical virtual reflected images created by the CG software include optical virtual arrow-shaped reflected images created by CG software in the respective cases of the presence and absence of the color filter when virtual light is incident from the crown side of the diamond and an optical virtual heart-shaped reflected image created by CG software in the case of the presence of the color filter when virtual light is incident from the pavilion side.

3. A method of preparing a diamond written expert opinion according to the present invention includes the steps of: reading a barcode including a management number of a diamond and measurement inspection company information and a two-dimensional code stored in a computer database by using a reader; taking a silhouette image of the diamond by a CCD camera in order to measure the dimensions of the diamond managed by the same management number; creating a three-dimensional shape image of the diamond by CG software on the basis of the diamond images which have been taken; and outputting and displaying an optical virtual reflected image from the flat surface side of the three-dimensional shape image created by the CG software on the basis of the three-dimensional shape image of the diamond and optical virtual reflected images depending on the presence or absence of the color filter when viewed from directly above with the bottom surface facing up in a display field of the written expert opinion.

* * * * *